US00PP15239P3

(12) United States Plant Patent
Gray

(10) Patent No.: US PP15,239 P2
(45) Date of Patent: Oct. 19, 2004

(54) *HYDRANGEA* HYBRID PLANT NAMED 'SWEET CAROL'

(50) Latin Name: *Hydrangea hybrid*
Varietal Denomination: Sweet Carol

(75) Inventor: Joseph Gray, Winters, CA (US)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 10/357,634

(22) Filed: Feb. 3, 2003

(65) Prior Publication Data

US 2004/0154062 P1 Aug. 5, 2004

(51) Int. Cl.[7] ..... A01H 5/00

(52) U.S. Cl. ..... Plt./250

(58) Field of Search ..... Plt./250

*Primary Examiner*—Bruce R. Campell
*Assistant Examiner*—Louanne Krawczewicz Myers
(74) *Attorney, Agent, or Firm*—Christie, Parker & Hale, LLP

(57) ABSTRACT

A new plant variety of *Hydrangea* hybrid characterized by its large lacecap inflorescence, which is reminiscent of its macrophylla lineage, while being substantially hardier than macrophylla cultivars; the white-eye zone on sterile inflorescences when young; deeply serrated leaves; and merlot colored fall foliage.

2 Drawing Sheets

Classification: *Hydrangea serrata×macrophylla* 'Lanarth White'×*Hydrangea serrata* 'Blue Billow'.

Varietal denomination: The new plant has the varietal denomination 'Sweet Carol'.

BACKGROUND OF THE INVENTION

The present invention relates to a new and distinct variety of *Hydrangea* hybrid, which was developed in a controlled breeding program in Silver Spring, Md., United States, by Mr. Joseph Gray.

The genus *Hydrangea* is included in the family *Saxifragaceae* which comprises about 80 genera and 1,200 species of herbs, shrubs, small trees and woody climbers mostly temperate in origin. *Hydrangea* comprises approximately 23 species of deciduous or evergreen shrubs and vines originating in North America, South America and East Asia, many of which possess desirable ornamental characteristics. Recent taxonomical treatments sometimes isolate *Hydrangea* in a new family, *Hydrangeaaceae.*

*Hydrangea macrophylla* is widespread and common throughout much of Japan. It generally has opposite, simple leaves, obovate to elliptic in shape, 10 to 20 cm long and 5 to 15 cm wide. Leaf color ranges from light to dark green, depending on light intensity and cultural conditions. Leaves are generally softly pubescent. Flower color is dependent upon the pH level of the soil and the amount of available aluminum in the soil media. Flowers of *Hydrangea macrophylla* are borne in mostly sterile florets, formed in what is often called a "hortensia" flower.

*Hydrangea serrata* is widespread and common throughout much of Japan, Korea and China. It generally has opposite, simple leaves, lanceolate in shape with acuminate apices, 5 to 15 cm long and 5 to 10 cm wide. Leaf color ranges from light to dark green, depending on light intensity and cultural conditions. Leaves are generally softly pubescent. The plant is deciduous. Flower color is dependent upon the pH level of the soil and the amount of available aluminum in the soil media. Flowers of *Hydrangea serrata* are borne in mostly flattened corymbs, 1 to 5 cm wide, with up to 12 sterile florets.

SUMMARY OF THE INVENTION

The new variety was discovered in a controlled breeding program of *Hydrangea serrata* and *H. serrata×macrophylla,* and differs from its parents in its large lacecap inflorescence, which is reminiscent of its macrophylla lineage, while being substantially hardier than macrophylla cultivars; the white-eye zone on sterile inflorescences when young; deeply serrated leaves; and merlot colored fall foliage. Asexual reproduction of the new variety by stem cuttings, performed in Silver Springs, Md. and Vacaville, Calif., have confirmed that the distinctive characteristics of the new variety are stable and transmitted to succeeding generations, and the new variety reproduces true to type.

COMPARISON WITH PARENTS

'Sweet Carol' is distinguished from its parents and all other varieties of *Hydrangea* of which I am aware in its large lacecap inflorescence, which is reminiscent of its macrophylla lineage, while being substantially hardier than macrophylla cultivars; the white-eye zone on sterile inflorescences when young; deeply serrated leaves, and merlot colored fall foliage.

COMPARISON WITH CLOSEST KNOWN CULTIVAR

The closest known cultivar to 'Sweet Carol' is *Hydrangea*×'Sweet Chris' (U.S. Patent Pending; Ser. No. 10/357,938). 'Sweet Carol' exhibits larger flower panicles and larger and more recurved outer florets than 'Sweet Chris'. Additionally, 'Sweet Carol' and 'Sweet Chris' differ in flower color, and the stems of 'Sweet Carol' are green as compared to the reddish colored stems of 'Sweet Chris'.

BRIEF DESCRIPTION OF ILLUSTRATIONS

The accompanying illustrations show a specimen of the new cultivar in a photo illustration as true to color as is reasonably possible to make in an illustration of this character. The plants shown in the photographic illustrations are 4-year-old plants in 5-gallon nursery containers.

DETAILED DESCRIPTION OF THE NEW VARIETY

Figure 1:
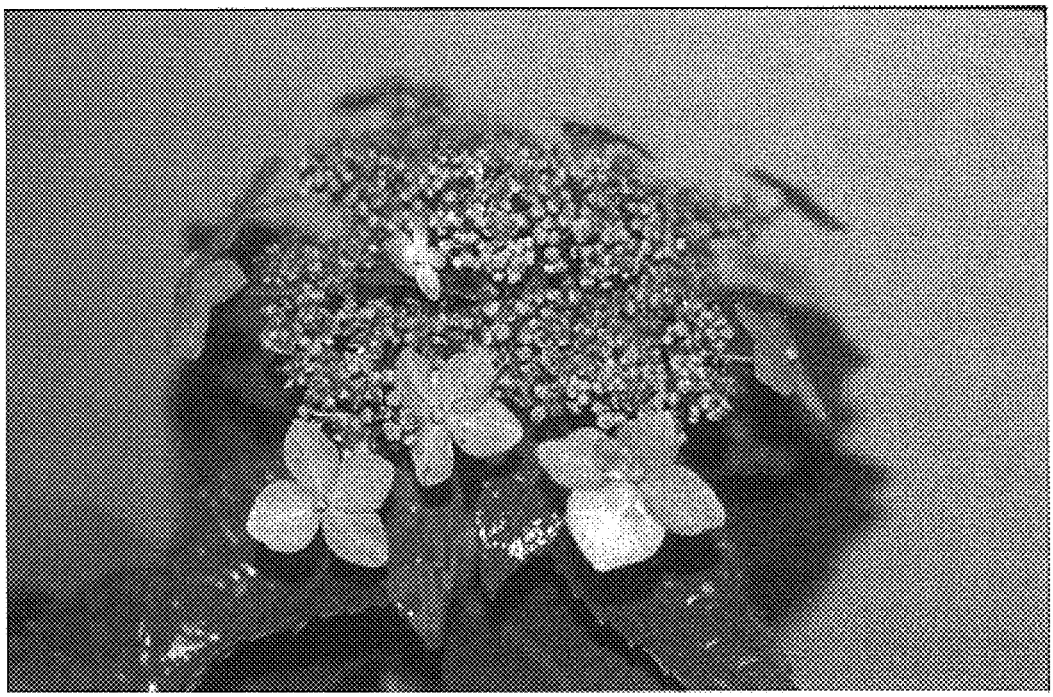
FIG. 1 illustrates the inflorescence and overall habit of 'Sweet Carol'.
Figure 2:
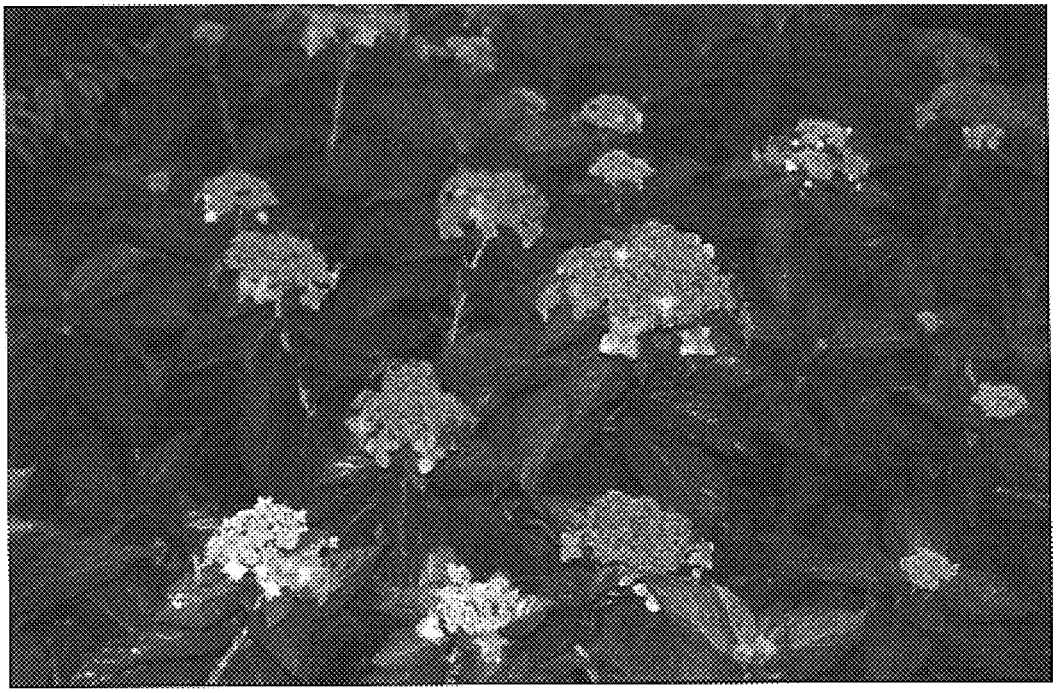
FIG. 2 illustrates the inflorescence of 'Sweet Carol'.

'Sweet Carol' has not been observed under all possible environmental, cultural and light conditions. The following observations and descriptions are of 4-year-old plants in 5-gallon nursery containers grown outdoors in Vacaville, Calif., under 50% shade, in a 6.6 pH soiless nursery growing media. In this description, color references are to The Royal Horticultural Society Colour Chart (2001) and terminology used in the color descriptions herein refers to plate numbers in this color chart. Phenotypic expression may vary with light intensity, cultural and environmental conditions.

Parentage:
- *Mother plant.*—*Hydrangea serrata×macrophylla* 'Lanarth White' (unpatented).
- *Father plant.*—*Hydrangea serrata* 'Blue Billow' (unpatented).

Propagation: By vegetative cuttings.

PLANT

Size: 1.5 to 2 meters tall and 1 to 1.5 meters wide.
Habit: Upright, compact shrub.
- *Typical number lateral branches.*—20.
- *Observed number lateral branches.*—20.
- *Typical branch length.*—To 40 cm.
- *Observed branch length.*—To 40 cm.
- *Branch diameter.*—From 5 to 7 mm.
- *Color of mature branches.*—Near Grey-Orange Group 177B.
- *Color of new branches.*—Near Green Group 143C.

Internodes:
- *Length.*—From 4 to 5 cm.
- *Color.*—Near Green Group 138B–C.

LEAF

Shape: Ovate to ovate lanceolate, cuneate to attenuate at the base and acuminate to long acuminate apices.
Leaf size: To 19 cm long and 8 cm wide.
Arrangement: Opposite.
Margin: Deeply serrated; serrations are up to 4 mm deep.
Substance: Thick, coriaceous, to slightly succulent.
Texture:
- *Underside.*—Glabrous, slightly glossy.
- *Upper side.*—Glabrous, dull to slightly glossy.

Venation: Opposite or alternately pinnate.
- *Underside.*—Raised.
- *Upper side.*—Impressed.
- *Color.*—New Foliage: Upper Surface: Near Yellow-Green Group 146B. Under Surface: Near Yellow-Green Group 144B. Mature Foliage: Upper Surface: Near Yellow-Green Group 146B. Under Surface: Near Yellow-Green Group 144B.

Leaf color:
- *Young foliage.*—Near Green Group 138B.
- *Mature foliage.*—Upper side: Near Green Group 139A. Underside: Near Green Group 138B–C.

Petioles:
- *Size.*—2.5 to 3 cm long.
- *Coloration.*—Near Green Group 138B–C.
- *Texture.*—Glabrous.

Hardiness: USDA Zone 6 (−10° F. to 0° F.).
Vigor: Vigorous growth.
Pests/diseases: No susceptibility or resistance to disease beyond that of the species has been noted.

INFLORESCENCE

*Bloom period.*—May–August.
*Inflorescence.*—Loose tiered corymb with both sterile (12), sepalous florets and fertile (650), non-sepalous florets borne on the same corymb.
*Shape of inflorescence.*—Umbel of numerous small florets, sepalous florets are flat.
*Inflorescence width.*—14 to 20 cm across.
*Typical number of inflorescence per lateral branch.*—1 to 3.
*Observed number of inflorescence per lateral branch.*—1.
*Flower arrangement.*—Loose tiered umbel 15 to 18 cm across (lace cap type).
*Fragrance.*—None.
*Lastingness of individual blooms.*—Flowers are very persistent, lasting up to 5 months. As the flowers mature, the pedicels bearing the outer florets bend to invert the florets toward the ground.

Peduncles:
- *Length.*—3.0 to 4.0 cm.
- *Diameter.*—1 to 2 mm.
- *Strength.*—Firm.
- *Angle.*—From parallel to 90 degrees to the ground plane.
- *Color.*—Near Green Group 138B–C.

Infertile florets:
- *Sepals.*—Usually 4, sometimes 5, sepals per floret, with one dominant sepal, 2 smaller equally sized sepals, and 1 yet smaller sepal.
- *Typical and observed sepal sizes.*—Dominant Sepal: To 30 mm wide and 22 mm long. Mid-sized Sepal: To 14 mm wide and 16 mm long. Small Sepal: To 8 mm wide and 11 mm long.
- *Margin.*—Entire except for 25% of margin at apex is dentately serrated.
- *Shape.*—Ovate.
- *Apex.*—Obtuse to acute.
- *Base.*—Shortly attenuate.
- *Curvature.*—Abaxial.
- *Arrangement.*—Overlapping at base.
- *Sepal color.*—Upper side: Near Red-Purple Group 62B at soil pH of 6.6. However, sepals can be variable in color, depending on the soil pH. Underside: Near Red-Purple Group 63A to 63B.
- *Pedicels.*—Length: 2.5 to 3.0 cm. Diameter: Approximately 1 mm. Strength: Firm. Angle: Parallel to ground plant. Color: Near Green Group 138B–C.

Fertile florets:
- *Size of floret.*—Approximately 1 mm in diameter.
- *Color of floret.*—Near Red-Purple Group 63B.
- *Pedicels.*—Length: 4 to 10 mm. Diameter: Less than 1 mm. Strength: Firm. Angle: From 5 to 45 degrees to ground plane. Color: Near Green Group 138B–C.

REPRODUCTIVE ORGANS

Androecium:

*Stamens.*—Approximately 7 to 10.

*Stamen filament color.*—Near Red-Purple Group 57C.

*Anthers.*—Quantity: 3. Shape: Club-shaped. Length: Less than 1 mm. Color: Near Orange-Greyed Group 165B.

*Pollen amount.*—Very little, not measurable.

*Pollen color.*—Near White Group 155D.

Gynecium:

*Pistils.*—Number: Usually 4; occasionally 3 or 5. Length: 2 mm.

*Stigmas.*—Quantity: Usually 4, occasionally 3 or 5. Shape: Rounded. Color: Near Red-Purple Group 57D.

*Styles.*—Number: 2 to 4, occasionally 5. Length: Less than 1 mm. Color: Near Red-Purple Group 57D.

*Ovaries.*—Quantity: 3 on each flower. Shape: Oval. Size: Less than 1 mm long. Color: Near Green Group 138B–C.

*Fruit.*—None noted.

I claim:

1. A new and distinct variety of *Hydrangea* hybrid plant, named 'Sweet Carol', substantially as shown and described.

* * * * *